United States Patent
Koike et al.

(10) Patent No.: US 7,067,140 B2
(45) Date of Patent: Jun. 27, 2006

(54) COSMETIC COMPOSITION

(75) Inventors: Kenzo Koike, Tokyo (JP); Masaki Shimizu, Tokyo (JP); Junichi Fukasawa, Tokyo (JP); Hiroshi Ota, Tokyo (JP); Tsutomu Fujimura, Tochigi (JP); Kazue Tsukahara, Tochigi (JP); Yuji Suzuki, Tokyo (JP)

(73) Assignee: Kao Corporation, Tokyo (JP)

( * ) Notice: Subject to any disclaimer, the term of this patent is extended or adjusted under 35 U.S.C. 154(b) by 46 days.

(21) Appl. No.: 10/211,589

(22) Filed: Aug. 5, 2002

(65) Prior Publication Data

US 2003/0017185 A1    Jan. 23, 2003

Related U.S. Application Data

(63) Continuation of application No. 09/289,634, filed on Apr. 12, 1999, now Pat. No. 6,461,623.

(30) Foreign Application Priority Data

Apr. 13, 1998  (JP) .................. 10-101076
Apr. 28, 1998  (JP) .................. 10-118716

(51) Int. Cl.
  *A61K 6/00*  (2006.01)
  *A61K 9/14*  (2006.01)

(52) U.S. Cl. ...................... 424/401; 424/489

(58) Field of Classification Search ......... 424/69, 424/70.1, 70.4, 70.11, 70.12, 401, 489, 78.02, 424/78.03
See application file for complete search history.

(56) References Cited

U.S. PATENT DOCUMENTS

| | | | | |
|---|---|---|---|---|
| 4,132,771 A | * | 1/1979 | Schreiber et al. ............. 424/52 |
| 4,159,316 A | * | 6/1979 | Januszewski et al. .......... 424/49 |
| 4,626,550 A | * | 12/1986 | Hertzenberg ................. 514/770 |
| 4,647,451 A | * | 3/1987 | Piechota, Jr. ................. 424/52 |
| 4,965,071 A | * | 10/1990 | Kawan ....................... 424/401 |
| 5,149,521 A | * | 9/1992 | Hirose et al. ................. 424/58 |
| 5,389,284 A | | 2/1995 | Van Der Hoeven et al. |
| 5,480,632 A | | 1/1996 | Orr et al. |
| 5,747,004 A | * | 5/1998 | Giani et al. ................... 424/49 |
| 5,904,735 A | | 5/1999 | Gutierrez et al. |
| 6,287,580 B1 | * | 9/2001 | Gott et al. ................... 424/401 |

FOREIGN PATENT DOCUMENTS

| | | |
|---|---|---|
| EP | 0 897 719 | 2/1999 |
| EP | 0 897 719 A1 * | 2/1999 |
| EP | 0 950 400 A2 | 10/1999 |
| JP | 54140740 A * | 11/1979 |
| JP | 09048715 A * | 2/1997 |
| JP | 9-151110 | 6/1997 |
| JP | 9-175925 | 7/1997 |
| KR | 329214 B * | 4/2002 |

OTHER PUBLICATIONS

Patent Abstracts of Japan, vol. 18, No. 337 (C-1217), Jun. 27, 1994, JP 06 080534, Mar. 22, 1994.
Chemical Abstracts, vol. 125, No. 2, Jul. 8, 1996, AN 18698, JP 08 059455, Mar. 5, 1996.

* cited by examiner

*Primary Examiner*—S. Tran
(74) *Attorney, Agent, or Firm*—Oblon, Spivak, McClelland, Maier & Neustadt, P.C.

(57) ABSTRACT

A non-aqueous cosmetic composition contains (A) activated zeolite, (B) a polyhydric alcohol having a molecular weight not higher than 1,000, and (C) a high molecular compound soluble in the ingredient (B). When shaken upon use, the cosmetic composition permits ready and even dispersion of the zeolite, exhibits good spreadability and compatibility on the skin and can be readily applied over a wide area. Moreover, the cosmetic composition also has excellent massaging effect.

9 Claims, No Drawings

COSMETIC COMPOSITION

BACKGROUND OF THE INVENTION a) Field of the Invention

This invention relates to a cosmetic composition capable of exhibiting good spreadability and compatibility and excellent massaging effect on the skin.

b) Description of the Related Art

Conventional cosmetic compositions for massaging aids include those with zeolite added to make use of its heat of hydration to give a calefacient feeling, and those with various powders added to make use of their scrubbing effect. Of these, the cosmetic compositions making use of zeolite (activated zeolite) which gives off heat upon hydration are known to include those disclosed in U.S. Pat. No. 3,250,680, Japanese Patent Application Laid-Open (Kokai) NO. SHO 61-204111, and Japanese Patent Application Laid-Open (Kokai) NO. HEI 6-100411. They are described as promoting blood circulation and offering good comfort during use owing to the heat of hydration of zeolite.

Such powdery substances, when remain precipitated over an extended time, undergo caking and become difficult to be redispersed. Hence, cosmetic compositions which contain these powdery substances are usually converted into gel systems by using thickeners so that the powdery substances remain evenly dispersed.

Such gelling of the systems however impairs their spreadability and compatibility on the skin, thereby making it difficult to apply them as body preparations to wide areas.

SUMMARY OF THE INVENTION

An object of the present invention is therefore to provide a cosmetic composition, which exhibits good spreadability and compatibility on the skin and permits easy application to the body surface over a wide area.

The present inventors have found that a non-aqueous cosmetic composition containing zeolite (activated zeolite), which gives off heat upon contact with water, a specific polyhydric alcohol and a high molecular compound readily permits even dispersion of zeolite when shaken upon use and moreover that the non-aqueous cosmetic composition exhibits good spreadability and compatibility on the skin, allows easy application to a wide area and also has excellent massaging effect. In addition, it has also been found that addition of a surfactant to the non-aqueous cosmetic composition makes it possible to obtain a cleansing agent also excellent in exothermicity and stability.

In one aspect of the present invention, there is thus provided a non-aqueous cosmetic composition comprising (A) activated zeolite, (B) a polyhydric alcohol having a molecular weight not higher than 1,000, and (C) a high molecular compound soluble in the ingredient (B).

In another aspect of the present invention, there is also provided a substantially non-aqueous detergent composition comprising (A) activated zeolite, (B) a polyhydric alcohol having a molecular weight not higher than 1,000, (C) a high molecular compound soluble in the ingredient (B), and (F) a surfactant.

The cosmetic composition according to the present invention, when brought into contact with water, provides a calefacient feeling owing to heat of hydration and also shows excellent massaging effect owing to the scrubbing effect of the powder. A comfortable warm feeling can be obtained, for example, when the cosmetic composition is applied on wet skin soaked with bathing or shower water. When shaken upon use, the cosmetic composition can evenly and readily disperse zeolite, exhibits good spreadability and compatibility on the skin and permits easy application to the body surface over a wide area. It can therefore be used as a cosmetic product for massaging purpose, e.g., a lotion, a cream, a toothpaste or an ointment.

On the other hand, the detergent composition which contains a surfactant can be used as a detergent or a cleansing agent including a garment detergent, a cleanser, a dish washing detergent, an automated dishwasher detergent, a car washing detergent, a tool detergent, a housecleaning agent, an antimold agent, a body washing composition, a shampoo, a face cleansing composition and a handwash. In particular, a body cleansing composition, a shampoo, a face cleansing composition and a handwash are suited.

DETAILED DESCRIPTION OF THE INVENTION AND PREFERRED EMBODIMENTS

No particular limitation is imposed on the activated (or exothermic) zeolite employed as the ingredient (A) in the present invention. From the viewpoints of availability and cost, preferred are those including zeolite 3A, zeolite 4A and zeolite 5A represented by the following general formula:

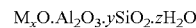

wherein M represents an alkali metal and/or an alkaline earth metal, and x, y and z stand for average numbers. Further, zeolite subjected to special treatments such as ion exchange treatment and neutralization treatment are also usable.

From the standpoints of the rate of hydration and feeling of use, these zeolites may preferably have particle sizes of from 0.1 to 200 μm, especially of from 1 to 100 μm.

These zeolites can be obtained by conducting production, purification, grinding, calcination and classification by methods known per se in the art. As disclosed in European Patent No. 187912 [Japanese Patent Application Laid-Open (Kokai) No. SHO 61-204111], zeolite of desired activity can be obtained by calcining and dehydrating raw zeolite at about 300 to 600° C. and then holding it in dry air.

Activated zeolite absorbs some amount of gas so that, when it is reacted with water, the gas is released. By the gas so released, a container with a composition filled therein may be caused to bulge. To avoid this potential problem, it is desired in the present invention to subject the activated zeolite to degasification treatment under heating or reduced pressure before mixing it with the other ingredients. As degasification conditions, it is preferred to conduct the degasification treatment at 70° C. or higher and 200 torr or lower (especially at 90 to 150° C. and 60 torr or lower) for 1 to 24 hours.

Whether or not the degasification procedure has been conducted sufficiently can be determined by measuring the gas adsorption of the zeolite. The gas adsorption can be measured by the method described, for example, in Japanese Patent Publication (Kokoku) No. HEI 8-5770. As an alternative, it can be measured by a method which comprises adding water to the zeolite itself or a zeolite-containing cosmetic in an amount twice as much as the zeolite in a sealed vessel to release gas and then measuring the quantity of the gas so released.

A gas adsorption of 2 ml/g or less, further 1 ml/g or less, notably 0.5 ml/g or less is preferred from the standpoint of prevention of gas release and container deformation.

Further, removal of gas can also be conducted by mixing the zeolite with ethanol. When the zeolite is zeolite 4A, for example, the amount of ethanol which can be adsorbed on the zeolite is theoretically about 30% of the weight of the zeolite. Therefore, it is preferred to mix 30 parts by weight or more of ethanol with 100 parts by weight-of the zeolite, with a zeolite/ethanol ratio of from 100/50 to 100/500 (weight ratio) being especially preferred.

To efficiently remove gas components, zeolite may be heated, depressurized or pressurized in the presence of ethanol. For heat treatment, 30° C. or higher, especially 50 to 90° C. is preferred. No particular limitation is imposed on the time of treatment, 1 hour to 3 days being practical. Ethanol having a purity of 95% or higher, notably 98% or higher, is preferred to be used.

From the viewpoints of exotherm property and spreadability of the composition, it is preferred to use zeolite in a proportion of from 1 to 60 wt. %, especially from 5 to 40 wt. %, typically from 10 to 30 wt. % in the cosmetic composition according to the present invention.

The polyhydric alcohol employed as the ingredient (B) in the present invention is one having a molecular weight not higher than 1,000. Many of polyhydric alcohols with molecular weight higher than 1,000 have high melting points and are unsuitable for use as a principal ingredient. However, it is not excluded to use them in small proportions.

No particular limitation is imposed on the polyhydric alcohol having a molecular weight not higher than 1,000 insofar as it is used commonly in cosmetics. Illustrative are alkylene glycols such as ethylene glycol, propylene glycol, butylene glycol, amylene glycol, isoprene glycol and hexylene glycol; dialkylene glycols such as diethylene glycol, dipropylene glycol, diethylene glycol monomethyl ether, diethylene glycol monoethyl ether; aliphatic triols such as glycerin; polyglycerins; polyethylene glycols; polypropylene glycols; ethylene oxide-propylene oxide copolymers, butyl monoethers of ethylene oxide-propylene oxide copolymers; and alkylene oxides including $C_1$–$C_5$ ethers such as glycerol adducts of polyethylene oxide, polypropylene oxide and poly(ethylene oxide-propylene oxide).

Of these, polyethylene glycol (molecular weight: 200–600), butylene glycol, isoprene glycol and glycerin are especially preferred from the standpoints of feeling of use and moisture retention.

These polyhydric alcohols can be used either singly or in combination. Preferred amount of such a polyhydric alcohol is from 1 to 95 wt. %, further from 5 to 90 wt. %, especially from 10 to 70 wt. % based on the whole composition because of good spreadability, good feeling of use and good touch.

The high molecular-compound (C) is soluble in the polyhydric alcohol (B). The term "soluble" as used herein means solubility of at least 0.01 wt. % based on the solvent. The term "high molecular" as used herein means a molecular weight of 2,000 or higher. This ingredient makes it possible to improve the redispersibility of powder such as zeolite in the non-aqueous system. Examples of such a high molecular compound include natural substances such as cellulose derivatives; and synthetic polymers such as copolymers of (meth)acrylic acid and its derivatives. As a commercial product, for example, "Carbopol ETD-2020", "Carbopol ETD-1382", "Carbopol ETD-1342", "Pemulen TR-1" and "Pemulen TR-2" (trade names; products of B. F. Goodrich Co.) are available.

Among these, particularly preferred are acrylic acid-methacrylic acid ester copolymers such as "Carbopol ETD-2020", "Pemulen TR-1" and "Pemulen TR-2", which have a structure represented by the following formula:

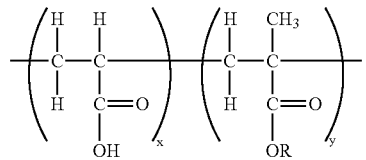

wherein R represents an alkyl group having 10 to 30 carbon atoms, X and Y represent mole % of corresponding units in the respective copolymers, X ranges from 80.0 to 99.9 mole %, and Y ranges from 0.1 to 20.0 mole %.

As the ingredient (C), such high molecular compounds can be used either singly or in combination. Preferred amount of such a high molecular compound is from 0.01 to 5 wt. %, further from 0.1 to 3 wt. %, especially from 0.1 to 2 wt. % based on the total amount of the composition, giving a cosmetic composition of good zeolite redispersibility.

Further, high molecular compounds insoluble in polyhydric alcohols, such as cellulose powder and nylon powder, can be used to an extent not impairing the effects of the present invention.

The cosmetic composition according to the present invention may be further added with the solid salt (D). By particles of this additional ingredient, scrubbing effect and skin contracting effect can be obtained. Examples of such a solid salt include alkali metal salts and alkaline earth metal salts, with sodium chloride and potassium chloride being especially preferred. These solid salts may preferably have particle size of from 0.01 to 3 mm, especially from 0.1 to 1.5 mm.

These solid salts can be used either singly or in combination. The preferred amount of the salt is from 0.1 to 30 wt. %, notably from 1 to 15 wt. % based on the whole composition to give a good feeling of scrubbing and contracting effect.

Moreover, the cosmetic composition according to the present invention may be further added with (E) a Fucus extract. This brings about still better skin contracting effect.

The term "Fucus extract" as the ingredient (E) means a solvent extract itself, a dilution or concentration of the extract; or dried powder obtained from the extract. It is obtained by grinding, either after or without drying, the whole weed or at least one of leaves, petioles, stems, roots and seeds of seaweed Fucus and then extracting it with a solvent at room temperature or under heating or extracting it with a Soxhlet apparatus.

Examples of the extracting solvent can include water, organic solvents and mixtures thereof. Preferred examples of the organic solvents can include hydrocarbons such as petroleum ether and cyclohexane; ethers such as diethyl ether; esters such as ethyl acetate; ketones such as acetone; alcohols such as ethanol, propanol, butanol, propylene glycol, butylene glycol and polyethylene glycol; and pyridine.

The extraction from the weed source may be carried out, for example, as follows. A solvent is added to the weed source or its dried product or dried ground product, followed by extraction at 1 to 100° C., preferably 3 to 70° C. for 0.5 to 30 days, preferably 1 to 15 days. The resulting extract solution is filtered, left over standstill or likewise processed as needed. The resulting extract may be further formed into powder or paste product by dilution, concentration or freeze-drying. Further, purification such as deodorization or decoloration may also be conducted as needed by a method known per se in the art. As the Fucus extract, a commercial product can also be used.

For the exhibition of the enough effect, it is preferred to add the Fucus extract in a proportion of from 0.0001 to 5 wt. %, notably from 0.001 to 1 wt. % in terms of a dry solid to the composition.

The cosmetic composition according to the present invention can be formulated into a non-aqueous detergent composition by additionally incorporating a surfactant as an ingredient (F).

No particular limitation is imposed on the surfactant as the ingredient (F) insofar as it is used in general detergent compositions. It may be either ionic (anionic, cationic or amphoteric) or nonionic, and may be used either singly or in combination. Specific examples include, as anionic surfactants, salts of $C_{12}$–$C_{20}$ fatty acids, alkyl ether sulfates, alkyl sulfate esters, alkyl benzenesulfonates, α-olefinsulfonates, monoalkyl phosphate esters and dialkyl phosphate esters; as cationic surfactants, "Sanisol" and "Quartamin" (trade marks, products of Kao Corporation); as amphoteric surfactants, "Anhitol" series (trade mark, products of Kao Corporation) and amino-acid-base surfactants; as nonionic surfactants, higher alcohols, alkyl saccharides, polyoxyethylene alkyl ethers, sugar alcohol-fatty acid esters, monoglycerides and diglycerides.

Among these surfactants, particularly preferred are those soluble in polyhydric alcohols and low in water content because they are readily formulated and are excellent in exothermicity and feeling of use.

Addition of the surfactant as the ingredient (F) in a proportion of from 1 to 50 wt. %, further from 2 to 30 wt. %, especially from 5 to 20 wt. % based on the whole composition is preferred because the resulting detergent composition is excellent in detergency and feeling of use.

A chelating agent or antioxidant can also be additionally incorporated in the cosmetic composition or detergent composition according to the present invention. This brings about a further improvement in stability. Specific examples include ethylenediaminetetraacetic acid (EDTA), hydroxydiethanephosphonic acid, and dibutylhydroxytoluene.

Addition of such a chelating agent or antioxidant in a proportion of from 0.0001 to 2 wt. %, especially from 0.01 to 1 wt. % based on the whole composition is preferred because the exothermicity can be maintained sufficiently during storage.

In addition to the ingredients described above, further ingredients commonly used in cosmetic composition can be added as desired to extents not impairing the effects of the present invention. They are, for example, oily ingredients, lubricants, humectants, preservatives, germicides, antiphlogistics, astringents, styptics, analgesics, vitamins and derivatives thereof, viscosity modifiers, foaming agents, refreshing agents, cooling agents, metal rust inhibitors, animal or plant extracts other than those described above, colors and perfumes.

The cosmetic composition or detergent composition according to the present invention can be formulated by mixing the above-described ingredients together in a usual manner, and is substantially non-aqueous. The term "substantially non-aqueous" as used herein does not exclude the existence of water at a lower content in the cosmetic composition. The cosmetic composition may contain some water as far as heat of hydration can be produced enough when it is brought into contact with external water.

For practical use, the temperature of the cosmetic composition of the present invention may preferably rise to as high as around 40° C. when mixed with an equal volume of water of 25° C.

Concerning the marketing form, a two-layer separation type in which the powder precipitates in a liquid medium while left over standstill is preferred. Upon use, the cosmetic composition is shaken or agitated to re-disperse the powder ingredient. When dispersed as an even mixture, the viscosity (as measured at 25° C. by a Brookfield type viscometer) may preferably be not higher than 5,000 mPa·s, notably from 500 to 2,000 mPa·s. Within this range, the cosmetic composition can be spread well on the skin and can be applied over a wide area.

A completely redispersed state can be ascertained by observing no precipitate remaining on a bottom of a transparent container; i.e., the cosmetic composition is mixed by shaking or agitating in the container and the container is then held upside down to observe he state of the bottom.

In the case of the two-layer separation type, a stirring ball can be placed in a container of the product. A stirring ball at least a surface layer of which is made of ceramics or TEFLON (trade mark) is preferred in view of influence from activated zeolite and inorganic salts. In addition to a ball made of ceramics or TEFLON, a stainless steel ball coated with ceramics of TEFLON may also be used. The preferred diameter of the stirring ball may range from 1 to 50 mm, especially from 5 to 25 mm because sufficient stirring is assured.

When storing the cosmetic composition or detergent composition according to the present invention in a container, use of a laminated resin container is preferred to maintain exothermic property of the activated zeolite and the polyhydric alcohol and also to protect the composition from influence of light and further to provide a satisfactory external appearance as a commercial product. Specifically, it is preferred to use a laminated resin container comprising two or more materials selected from high-density polyethylene (HDPE) resin, ethylene-vinyl alcohol (EVOH) resin, polypropylene (PP) resin, polyethylene terephthalate (PET) resin, TEFLON resin, nylon resin, metallic aluminum, glass and ceramics. Among them, a laminated resin container made of HDPE resin, EVOH resin and PP resin is preferred, with a container additionally including a metallic aluminum layer added further therein is particularly preferred.

The present invention is described further based on Examples. It should however be borne in mind that the present invention is not limited to these Examples.

EXAMPLE 1

(Formulation Procedures)

1. Degasification of Zeolite

Twenty parts by weight of zeolite [water content: 5% max., "Zeolum A4 Powder" (trade name), product of TOSOH CORPORATION] were heated and degasified for 2 hours over an oil bath of 150° C. under stirring at 50 rpm in a 2-kg agitating homomixer equipped with a glass jacket while maintaining the internal pressure at 60 torr or lower by a vacuum pump.

2. Preparation of a "Pemulen" Phase

Polyethylene glycol 400 (50.5 parts by weight) was mixed with 5 parts by weight of glycerin and 11 parts by weight of 1,3-butylene glycol, followed by the mixing at room temperature with a suspension consisting of 0.5 part by weight of "Pemulen TR-1" and 3 parts by weight of silicone oil. The resulting mixture was stirred at 1,500 rpm for 10 minutes in a dispersion mill. The thus-obtained solution was heated to 80° C., at which the solution was maintained for 30 minutes under stirring at 100 rpm.

3. Mixing and Cooling

To the zeolite degasified by step 1, the liquid phase prepared in step 2 was added while maintaining the reduced pressure. They were mixed together by stirring at 50 to 100 rpm in the agitating homomixer. Further stirring (at 7,000 rpm) in the homomixer was conducted for 10 minutes, and the resulting mixture was cooled to 40° C.

4. Additives

To the slurry prepared in step 3, sodium chloride (average particle size: 0.5 mm) and a small amount of perfume, stabilizer and surfactant were added in a total amount of 10 parts by weight. The resultant mixture was stirred and mixed again. It was then cooled to room temperature, so that the formulation was completed.

The viscosity of the cosmetic composition formulated was 1,000 mPa·s at 25° C.

(Evaluation Upon Use)

Using commercial body gels (wash-away type, viscosity: 80,000 to 100,000 mPa·s) as controls, the feelings of use of the invention product and the commercial products were evaluated by 10 panellers with respect to the ease of applying to the body, spreadability and compatibility, and were ranked by the following standards:

A: Six or more panellers out of the 10 had good feeling.
B: Three to five panellers out of the 10 had good feeling.
C: Two or fewer panellers out of the 10 had good feeling.

(Measurement of Maximum Temperature Attained when Mixed with Water)

Further, each sample was mixed with an equal volume of water (25° C.) in a beaker, and subsequent temperature changes were recorded. Maximum temperatures so attained are also shown in Table 1.

TABLE 1

|  | Invention Product 1 | Commercial Product A | Commercial Product B |
| --- | --- | --- | --- |
| Viscosity (mPa · s, 25° C.) | 1,000 | 100,000 | 80,000 |
| Ease of applying | A | B | B |
| Spreadability | A | B | B |
| Compatibility | A | B | B |
| Attained maximum temperature | 38° C. | 26° C. | 25° C. |

It is clearly shown from the above results that Invention product 1 provides a good feeling of use.

EXAMPLE 2

A cosmetic composition was formulated in a similar manner as in Example 1 except that 0.8 part by weight of "Pemulen TR-2" was added in place of 0.5 part by weight of "Pemulen TR-1".

Comparative Product 1

A cosmetic composition was formulated in a similar manner as in Example 1 without addition of "Pemulen TR-1".

Comparative Product 2

A composition was formulated in a similar manner as in Example 1 except that sodium polystyrenesulfonate (polymerization degree: 50) which is soluble in the polyhydric alcohol solvent was added in place of "Pemulen TR-1".

Comparative Products 1 and 2 and Invention Products 1 and 2 were evaluated in redispersibility.

TABLE 2

|  | Added high molecular compound | Redispersibility of product after left over standstill for 1 week |
| --- | --- | --- |
| Invention Product 1 | "Pemulen TR-1" (soluble in polyhydric alcohol) | Readily redispersed when shaken about 10 times. |
| Invention Product 2 | "Pemulen TR-2" (soluble in polyhydric alcohol) | Readily redispersed when shaken about 10 times. |
| Comparative Product 1 | Not added | Not redispersed even after shaken as many as 30 times. |
| Comparative Product 2 | Sodium polystyrenesulfonate (insoluble in polyhydric alcohol) | Not redispersed even after shaken as many as 30 times. |

It is envisaged from the above results that the invention products, each of which contained the corresponding high molecular compound soluble in the polyhydric alcohol, are excellent in redispersibility.

EXAMPLE 3

Massaging aids of the formulas shown in Table 3 were formulated by usual procedures. They were used, and their skin contracting effects and feelings of use were evaluated. The results are also presented in Table 3.

(Evaluation Method)

By 10 Japanese women whose ages ranged from 22 to 38 years old, each massaging aid was applied on upper arms once a day while moisture remained there after bathing, followed by massaging. After these procedures were conducted over 6 weeks without a break, their feelings of skin contraction were organoleptically evaluated and were ranked in accordance with the below-described standards. Concerning the feeling of use, their feelings of smoothness were organoleptically evaluated and were ranked in accordance with the following standards.

(Ranking Standards)

(1) Skin Contracting Effect
A: Eight or more volunteers out of the 10 had a feeling of contraction.
B: Six to seven volunteers out of the 10 had a feeling of contraction.
C: Three to five volunteers out of the 10 had a feeling of contraction.
D: Two or fewer volunteers out of the 10 had a feeling of contraction.

(2) Feeling of Use (Feeling of Smoothness)
A: Eight or more volunteers out of the 10 had a feeling of smoothness.
B: Six to seven volunteers out of the 10 had a feeling of smoothness.

C: Three to five volunteers out of the 10 had a feeling of smoothness.

D: Two or fewer volunteers out of the 10 had a feeling of smoothness.

TABLE 3

| Ingredient (wt. %) | Invention Product 3 | Invention Product 4 | Comp. Product 3 |
|---|---|---|---|
| Glycerin | 5 | 5 | 5 |
| Polyethylene glycol 400 | 36 | 39 | 59 |
| 1,3-Butylene glycol | 15 | 15 | 20 |
| Acrylic acid-alkyl methacrylate copolymer ("Pemulen TR-1", product of B. F. Goodrich Co.) | 1 | 1 | 1 |
| Zeolite (product of TOSOH CORP.)* | 25 | 25 | — |
| Fucus extract (product of Ichimaru Pharcos Co., Ltd.) | 3 | — | — |
| Sodium chloride (average particle size: 0.5 mm) | 10 | 10 | 10 |
| Ethanol | 5 | 5 | 5 |
| Total | 100 | 100 | 100 |
| Skin contracting effect | A | B | C |
| Feeling of use (feeling of smoothness) | B | B | C |

*Used after degasified in a similar manner as in Example 1.

EXAMPLE 4

Detergent compositions of the formulas presented in Table 4 were formulated.

(Formulation Procedures)

1. Zeolite [water content: 5% max, "Zeolum A4 Powder" (trade name), product of TOSOH CORPORATION] was degasified in a similar manner as in Example 1.
2. Polyhydric alcohols (polyethylene glycol 400, glycerin, 1,3-butylene glycol), high molecular compounds ("Pemulen TR-l", etc.) soluble in the polyhydric alcohols and surfactants were mixed at room temperature, followed by stirring at 1,500 rpm for 10 minutes in a dispersion mill. The resulting solution was heated to 80° C., at which the solution was heated under stirring at 100 rpm for 30 minutes.
3. To the zeolite degasified by step 1, the liquid phase prepared in step 2 was added while maintaining the reduced pressure. They were mixed together by stirring at 50 to 100 rpm in the agitating homomixer. Further stirring (at 7,000 rpm) in the homomixer was conducted for 10 minutes, and the resulting mixture was cooled to 40° C.
4. To the slurry prepared in step 3, a perfume, sodium chloride, and chelating agents or stabilizers were added, followed by stirring again. It was then cooled to room temperature, so that the formulation was completed to obtain detergent compositions.

TABLE 4

| Ingredient (wt. %) | Invention Product 5 | Invention Product 6 | Invention Product 7 | Comp. Product 4 |
|---|---|---|---|---|
| (Zeolite) "Zeolum A-4" (product of TOSOH CORP.) | 23 | 23 | 23 | 23 |
| (Polyhydric alcohols) | | | | |
| Polyethylene glycol 400 | Balance | Balance | Balance | Balance |
| Glycerin | 5 | 5 | 5 | 5 |
| 1,3-Butylene glycol | 15 | 15 | 15 | 15 |
| (High molecular compounds soluble in polyhydric alcohols) | | | | |
| Acrylic acid-methacrylic acid copolymer ("Pemulen TR-1", product of B. F. Goodrich Co.) | 0.5 | — | 0.5 | — |
| Acrylic acid-methacrylic acid copolymer ("Pemulen TR-2", product of B. F. Goodrich Co.) | — | 0.8 | — | — |
| (Surfactants) | | | | |
| Lauric acid | — | 1.5 | 1.5 | — |
| Sorbitan coconut fatty acid ester | 3 | 2.5 | 2.5 | 3 |
| Polyethylene glycol monolaurate (EO12) | 2 | — | — | 2 |
| Lauroyl amide propylbetaine | 0.50 | 1.00 | 1.00 | 0.50 |
| Lauryl phosphate | 0.5 | 3 | 3 | 0.5 |
| Polyoxyethylene(2) sodium laurylsulfate | 0.50 | 1.00 | 1.00 | 0.50 |
| (Solid salt) | | | | |
| Sodium chloride | 5 | 5 | 5 | 5 |
| (Chelating agents or antioxidants) | | | | |
| Disodium ethylenediamineteraacetate | 0.4 | 0.4 | 0.4 | 0.4 |
| Hydroxyethanediphosphonic acid | 0.2 | 0.2 | 0.2 | 0.2 |
| Dibutylhydroxytoluene | 0.5 | 0.5 | 0.5 | 0.5 |
| Perfume | q.v. | q.v. | q.v. | q.v. |

Test (Evaluation of Dispersibility)

The detergent compositions obtained in Example 4 were placed in glass bottles and were then left over standstill at room temperature for 1 week. All the solutions were of the two-layer separation type with powders precipitated. They were shaken up and down to evaluate their redispersibilities. The detergent compositions as Invention Products 5 to 7 were readily redispersible, whereas in Comparative Product 4, the powder underwent caking and was unreadily redispersible.

Japanese Patent Application Nos. 10-101076, 10-101077, 10-101078 and 10-101079, filed on Apr. 13, 1998, Japanese Patent Application Nos. 10-118716 and 10-118713, filed on Apr. 28, 1998, are incorporated herein by reference.

The invention claimed is:

1. A non-aqueous massaging aid comprising
   (A) 5 to 60 wt. % of an activated zeolite,
   (B) 10 to 70 wt. % of a polyhydric alcohol having a molecular weight not higher than 1,000,
   (C) a high molecular compound soluble in said ingredient (B),
   (D) a solid salt having particle sizes in a range of from 0.1 mm to 3 mm, and a silicone oil, wherein
   the high molecular compound has a molecular weight of 2000 or higher;
   the massaging aid separates, when at a standstill, into two layers as solids in the massaging aid precipitate into one of the layers; and
   the massaging aid has, when the solids are evenly dispersed in the massaging aid, a viscosity in a range of from 500 to 2000 mPa·s at 25° C.

2. The massaging aid according to claim 1, further comprising (E) a Fucus extract.

3. The massaging aid according to claim 1, which comprises the polyhydric alcohol in an amount of from 5 to 90 wt. % of said massaging aid, and the high molecular compound in an amount of from 0.1 to 3 wt. % of said massaging aid, and which further comprises a surfactant in an amount of 0 to 9 wt. % of said massaging aid.

4. The massaging aid according to claim 1, wherein the solid salt (D) is selected from sodium chloride and potassium chloride.

5. The massaging aid according to claim 1, wherein the activated zeolite is a powder.

6. The massaging aid according to claim 5, wherein the powder comprises particles having sizes in a range of from 0.1 to 200 μm.

7. The massaging aid according to claim 1, wherein the massaging aid is not a gel.

8. The massaging aid according to claim 1, wherein the massaging aid comprises from 0.1 to 30 wt. % of the solid salt (D).

9. The massaging aid according to claim 1, wherein the massaging aid comprises from 1 to 15 wt. % of the solid salt (D).

* * * * *